United States Patent
Cohen (10) Patent No.: US 10,152,512 B2
(45) Date of Patent: *Dec. 11, 2018

(54) METADATA-DRIVEN PROGRAM CODE GENERATION FOR CLINICAL DATA ANALYSIS

(71) Applicant: Accenture Global Solutions Limited, Dublin (IE)

(72) Inventor: Barry R. Cohen, Bryn Mawr, PA (US)

(73) Assignee: Accenture Global Solutions Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 15/795,562

(22) Filed: Oct. 27, 2017

(65) Prior Publication Data

US 2018/0181620 A1    Jun. 28, 2018

Related U.S. Application Data

(63) Continuation of application No. 15/392,956, filed on Dec. 28, 2016, now Pat. No. 9,842,139.

(51) Int. Cl.
*G06F 9/44* (2018.01)
*G06F 17/30* (2006.01)
(Continued)

(52) U.S. Cl.
CPC ......... *G06F 17/30477* (2013.01); *G06F 8/30* (2013.01); *G06F 17/30539* (2013.01);
(Continued)

(58) Field of Classification Search
CPC ..... G06F 8/20; G06F 8/33; G06F 8/38; G06F 17/30477; G06F 17/30544;
(Continued)

(56) References Cited

U.S. PATENT DOCUMENTS 6,925,391 B1 * 8/2005 Pesce ............... G01N 35/00603
                                                                702/21
7,246,134 B1 * 7/2007 Kitain ................. G06F 17/2247
(Continued)

OTHER PUBLICATIONS

'www.cdisc.org' [online]. "Analysis Data Model (ADaM)," Feb. 12, 2016, Retrieved from the Internet: URL <https://www.cdisc.org/standards/foundational/adam> 5 pages.
(Continued)

*Primary Examiner* — Ziaul A Chowdhury
(74) *Attorney, Agent, or Firm* — Fish & Richardson P.C.

(57) ABSTRACT

Techniques are described for metadata-driven code generation to generate code for analyzing data from clinical trial(s). A code generation engine may generate program code based on metadata that is input to the engine. The metadata may describe the data to be input to the generated code, and one or more artifacts to be output by the generated code on execution. The metadata may also describe one or more operations to be performed on the input data and/or intermediate data. The metadata may include one or more of the following: inline code to be included in the generated code; references to stored code to be included in the generated code; and/or instructions to be run to generate the code. Artifact(s) may include, but are not limited to, reports such as tables, figures, and/or listings that describe the results of analyzing or otherwise processing the data by the generated program code.

18 Claims, 5 Drawing Sheets

(51) Int. Cl.
    *G06F 8/30*    (2018.01)
    *G16H 10/20*   (2018.01)
    *G06F 19/00*   (2018.01)
(52) U.S. Cl.
    CPC ........ *G06F 17/30554* (2013.01); *G06F 19/00* (2013.01); *G16H 10/20* (2018.01)
(58) Field of Classification Search
    CPC ........ G06F 17/30539; G06F 17/30554; G06F 8/30; G06F 19/00; G16H 10/20
    See application file for complete search history.

(56) References Cited

U.S. PATENT DOCUMENTS

| | | | | |
|---|---|---|---|---|
| 8,682,925 | B1* | 3/2014 | Marquardt | G06F 17/30477 707/770 |
| 2004/0073463 | A1* | 4/2004 | Helms | G06F 19/3443 705/3 |
| 2004/0078364 | A1* | 4/2004 | Ripley | G06F 17/30477 |
| 2004/0172447 | A1* | 9/2004 | Miller | G16H 10/20 709/203 |
| 2005/0071801 | A1 | 3/2005 | Jesse | |
| 2006/0010110 | A1* | 1/2006 | Kim | G06F 17/30539 |
| 2006/0178778 | A1 | 8/2006 | Fuhlbrigge | |
| 2006/0178918 | A1 | 8/2006 | Mikurak | |
| 2009/0049040 | A1* | 2/2009 | Fay | G06F 17/30734 |
| 2009/0083703 | A1 | 3/2009 | Grady | |
| 2009/0093709 | A1 | 4/2009 | Patel | |
| 2009/0199213 | A1* | 8/2009 | Webster | G06F 8/34 719/320 |
| 2010/0083351 | A1 | 4/2010 | Ryder | |
| 2010/0242015 | A1* | 9/2010 | Stenberg | G06F 8/30 717/106 |
| 2010/0268544 | A1 | 10/2010 | Nitahara | |
| 2010/0268551 | A1 | 10/2010 | McNames | |
| 2012/0078648 | A1* | 3/2012 | Reiner | G06F 19/00 705/2 |
| 2012/0191749 | A1 | 7/2012 | New | |
| 2012/0227028 | A1 | 9/2012 | Pun | |
| 2013/0167114 | A1 | 6/2013 | Eska | |
| 2013/0238351 | A1* | 9/2013 | Burns | G06F 19/363 705/2 |
| 2014/0143719 | A1 | 5/2014 | Arazi | |
| 2014/0172827 | A1 | 6/2014 | Nos | |
| 2014/0222862 | A1* | 8/2014 | Arling | G06F 17/30477 707/769 |
| 2014/0316822 | A1* | 10/2014 | Kleeman | G06Q 10/00 705/3 |
| 2014/0365519 | A1* | 12/2014 | Middelfart | G06F 17/30477 707/769 |
| 2015/0074565 | A1* | 3/2015 | Roche | G06F 17/30554 715/763 |
| 2015/0277881 | A1 | 10/2015 | Strehovsky | |
| 2015/0286802 | A1 | 10/2015 | Kansara | |
| 2015/0351673 | A1 | 12/2015 | Vanslyke | |
| 2016/0004749 | A1* | 1/2016 | Hanaoka | G06F 17/30554 707/722 |
| 2016/0019268 | A1 | 1/2016 | Patel | |
| 2016/0063062 | A1* | 3/2016 | Yahav | G06F 17/30477 707/769 |
| 2016/0109526 | A1 | 4/2016 | Geffin | |
| 2016/0267110 | A1 | 9/2016 | deValk | |
| 2016/0274867 | A1 | 9/2016 | Narayanan | |
| 2016/0292066 | A1* | 10/2016 | Stevens | G06F 11/3624 |
| 2017/0286456 | A1* | 10/2017 | Wenzel | G06F 17/30294 |
| 2017/0315784 | A1* | 11/2017 | Sarferaz | G06F 17/30554 |
| 2018/0203857 | A1* | 7/2018 | Fischer | G06F 17/3053 |

OTHER PUBLICATIONS

Fanny Lalonde Levesque et al., "A Clinical Study of Risk Factors Related to Malware Infections", [Online], 2013, pp. 97-108, [Retrieved from Internet on Oct. 13, 2017], <http://delivery.acm.org/10.1145/2520000/2516747/p97-levesque.pdf>.

Graciela Rosemblat et al., "A Pragmatic Approach to Summary Extraction in Clinical Trials", [Online], 2006, pp. 124-125, [Retrieved from Internet on Oct. 13, 2017], <http://delivery.acm.org/10.1145/1570000/1567648/p124-rosemblatpdf>.

Jonathan Sharp et al., "An Application Architecture to Facilitate Multi-Site Clinical Trial Collaboration in the Cloud", [Online], 2011, pp. 64-68, [Retrieved from Internet on Oct. 13, 2017], <http://delivery.acm.org/10-1145/1990000/1985511//p64-sharp.pdf>.

Fatih Altiparmak, "Relationship Preserving Feature Selection for Unlabelled Clinical Trials Time-Series", [Online], 2010, pp. 7-16, [Retrieved from Internet on Oct. 13, 2017], <http://delivery.acm.org/10.1145/1860000/1854784/p7-altiparmak.pdf>.

Extended European Search Report issued in European Application No. EP17209526, dated May 18, 2018, 6 pages.

Office Action issued in Australian Application No. 2017279795, dated May 17, 2018, 4 pages.

* cited by examiner

METADATA-DRIVEN PROGRAM CODE GENERATION FOR CLINICAL DATA ANALYSIS

CROSS-REFERENCE TO RELATED APPLICATION

The application is a continuation of U.S. patent application Ser. No. 15/392,956, filed on Dec. 28, 2016, entitled "Metadata-Driven Program Code Generation For Clinical Data Analysis," the entirety of which is incorporated by reference into the present application.

BACKGROUND

Clinical trials to test new drugs, medical devices, and/or treatment regimens are traditionally conducted using a large population of test subjects, and may generate a large amount of data to be analyzed. Traditionally, software is manually written to analyze the data and produce reports. For each new trial, new software programs may need to be written to analyze the newly collected data. Only limited efficiencies can be gained from using standard artifacts that are reused from study to study, given that the studies may be sufficiently different in the data being analyzed and the artifact(s) being output. Accordingly, analyzing the data generated through a series of clinical trials has traditionally been an inefficient process that consumes a large amount of computing resources and computer programmer time to code and execute software.

SUMMARY

Implementations of the present disclosure are generally directed to clinical data analysis. More particularly, implementations of the present disclosure are directed to generating, based on metadata, program code that is used to analyze clinical data and create artifacts such as reports.

In general, innovative aspects of the subject matter described in this specification can be embodied in methods that include actions of: accessing metadata that describes an input data set for a clinical trial, at least one artifact to be provided as output, and at least one operation to be performed on the input data set to create the at least one artifact; generating, based on the metadata, program code that performs the at least one operation to create the at least one artifact, wherein the generating of the program code includes one or more of executing at least one instruction included the metadata to generate at least a portion of the program code, retrieving at least a portion of the program code from a code repository based on a reference included in the metadata, or retrieving at least a portion of the program code that is included, inline, in the metadata; executing the program code, the executing comprising performing the at least one operation on the input data set, wherein the executing of the program code creates the at least one artifact based on the performing the at least one operation; and communicating the at least one artifact for presentation through a user interface of a computing device.

These and other implementations can each optionally include one or more of the following innovative features: the at least one artifact includes at least one of a table, a figure, or a listing of data; the at least one operation includes retrieving, from an electronic data capture (EDC) system, the input data set that includes raw data generated through the clinical trial, performing a quality check on the raw data, determining analysis data based on the raw data, and/or determining the at least one artifact based on the analysis data; the at least one operation further includes transforming the raw data to a first standard format and transforming the analysis data to a second standard format; the program code is associated with an individual study performed during the clinical trial; the input data set includes data associated with the individual study; the at least one artifact generated that is through execution of the program code is associated with the individual study; the program code is generated and executed by a same code generation engine; the actions further include storing at least a portion of the program code in a library that is accessible by the code generation engine for subsequent program code generation; and/or the metadata is arranged hierarchically to include at least two of global metadata that is associated with a plurality of studies, project level metadata that is associated with a project that includes a subset of the plurality of studies, or study level metadata that is associated with one of the plurality of studies.

Other implementations of any of the above aspects include corresponding systems, apparatus, and computer programs that are configured to perform the actions of the methods, encoded on computer storage devices. The present disclosure also provides a computer-readable storage medium coupled to one or more processors and having instructions stored thereon which, when executed by the one or more processors, cause the one or more processors to perform operations in accordance with implementations of the methods provided herein. The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

Implementations of the present disclosure provide one or more of the following technical advantages and improvements over traditional systems. Through use of a code generation engine to generate program code employed in analyzing data generated through clinical trials, implementations provide higher quality, more consistent, and more reliable program code than that generated through traditional techniques. Moreover, the metadata that is developed to instruct the code generation engine may also provide a complete, clear, and readily-available trace of the provenance of the collected data and/or derived data, as well as the analyses conducted during the clinical trial. Accordingly, systems that employ the implementations described herein consume less processing capacity, memory, storage, network capacity, and/or other computing resources compared to traditional systems that may require frequent re-coding and/or re-execution of code to achieve adequate results, and/or compared to traditional systems in which further coding and/or execution may be required to determine the provenance of data and/or analyses.

It is appreciated that aspects and features in accordance with the present disclosure can include any combination of the aspects and features described herein. That is, aspects and features in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the

DETAILED DESCRIPTION

Implementations of the present disclosure are directed to systems, devices, methods, and computer-readable media for metadata-driven code generation to generate software that is used for analyzing data generated through clinical trial(s). In some implementations, a code generation engine is employed to generate executable program code based on metadata that is input to the engine. The metadata may include various instructions that describe the data to be input to the generated code, and one or more artifacts to be output by the generated code on execution. The metadata may also describe one or more operations to be performed on the input data, and/or to be performed on intermediate data generated by previous operation(s). In some instances, intermediate data may exclude data that is generated by a final operation and/or data that is output for consumption by user(s). Artifact(s) may include reports such as tables, figures, and/or listings that describe the results of analyzing or otherwise processing the data by the program code. Artifacts may include new data (e.g., reformatted and/or derived data). Artifacts may also include data check reports produced through the checking of data (e.g., raw data, analysis data, and/or intermediate data). Artifacts may also include other types of reports, such as reports that describe the results of analysis.

In some implementations, one or more of the following tasks are performed for a clinical trial: verify the collected data through data check reports; transform the collected data to a structure that is analysis-ready and/or submission-ready; derive analysis data from the collected data; and/or compute analysis results and present them in one or more analysis reports.

The metadata may include one or more references to code in a code library, such that processing the metadata to generate the program code may include retrieving the referenced code from the library and adding it (e.g., as-is) to the generated program code. At least some referenced code may be self-configurable code. The reference(s) to this type of code may include parameters that instruct the code to configure itself in a particular way based upon the particular values of the parameters, as the code is added to the generated program code. The metadata may also include inline code to be included in the generated program code, such that processing the metadata to generate the program code may include retrieving the code from the metadata and adding it to the generated program code. In some instances, the code that is included inline in the metadata may be added to the library, such that subsequently processed metadata may reference the code in the library instead of including the code inline in the metadata. In some instances, a first set of metadata may be provided to generate code to analyze data and output a first set of artifacts, e.g., for a first clinical trial. Then, for a second set of artifacts to be generated, e.g., for a second clinical trial, the metadata may be prepared that describes the new artifacts and the second set of metadata may be used to generate new program code to analyze the new data. Accordingly, use of the metadata to generate code may facilitate the coding and/or re-coding process. For example, for the new study adjustments may be made to the metadata to generate the appropriate program code, instead of re-coding the entire set of program code to perform the new analysis. The code generation engine is configured to generate the program code based on the provided metadata. For example, a minor modification can be made to the metadata to generate new program code, and the minor modification may require less time and/or computing resources than conventional re-coding techniques.

Implementations described herein provide clinical data development services, such as automatic code generation for analyzing trial data generated through one or more clinical trials. Implementations provide an automated metadata driver that receives metadata instructions describing how to generate program code that executes to create artifact(s) (e.g., analysis reports, intermediate and/or analysis data, etc.) through analysis of the data. A code generation engine generates the program code based on the instructions included in the metadata. When artifacts are to be created for a study, the metadata may be provided to the code generation engine which generates and executes the program code to create the artifacts. Implementations may generate program code to output various artifact types, including but not limited to artifact data types and artifact report types. Artifact data types may include: tabulation data that is a representation of the data generated during a trial (e.g., in SDTM format); and/or analysis data derived from the collected raw input data (e.g., in ADaM format). Artifact report types may include: reports that describe the result of cleaning, checking, and/or formatting the data at various stages in its handling (e.g., check reports); and/or output reports such as tables, figures, and listings.

The program code generated by the engine may be of higher quality, higher performing, and/or with fewer bugs than code written manually. The generated code may be consistent across multiple code generation instances, given that the engine may consistently generate the same code in response to receiving the same metadata as input. Moreover, in at least some instances when a new artifact is to be created, new metadata is created, and this metadata may be validated. Validating the new metadata consumes significantly less time and resources compared to validating a new manually written program, as in conventional environments.

In some implementations, the code generation may be employed in a double programming scenario. Traditionally, clinical trial code development may employ a double programming regimen for quality assurance, in which two separate programmers (or teams of programmers) manually write the code needed to produce the same artifact. The two programs may then be executed and checked to ensure that they produce the same output. Using implementations described herein, one of the programmers in the traditional scenario may be replaced with the code generation engine. As a quality check, the output of the program code generated by the engine may be compared to the output of code that is manually written. In some scenarios, the program code automatically generated by the engine may be used without the need for the traditionally double programmed code, and the metadata may instead be inspected for quality prior to code generation. In such instances, the artifact(s) that are created may also be checked for quality. Double programming is a measurable effort that traditionally impacts clinical studies. Traditional double programming may consume a substantial amount of time and cost, and may generate sub-optimal code. The use of code generation according to implementations described herein may lead to the generation of higher quality code, and may enable traditional double programming techniques to be omitted, providing for a more efficient and cost-effective allocation of resources.

Implementations facilitate the generation of code that produces new and/or different artifact(s) compared to previously generated artifact(s). New artifacts can be expressed through metadata and generated using pre-validated code, such as previously generated and stored library code routines. To generate different artifacts, a (e.g., minor) change may be made to the metadata that is input to the engine, instead of requiring a full rewrite of the analysis program. Code generation through the implementations described herein may provide a substantial (e.g., 30-50%) cost savings compared to traditional methods.

Figure 1:
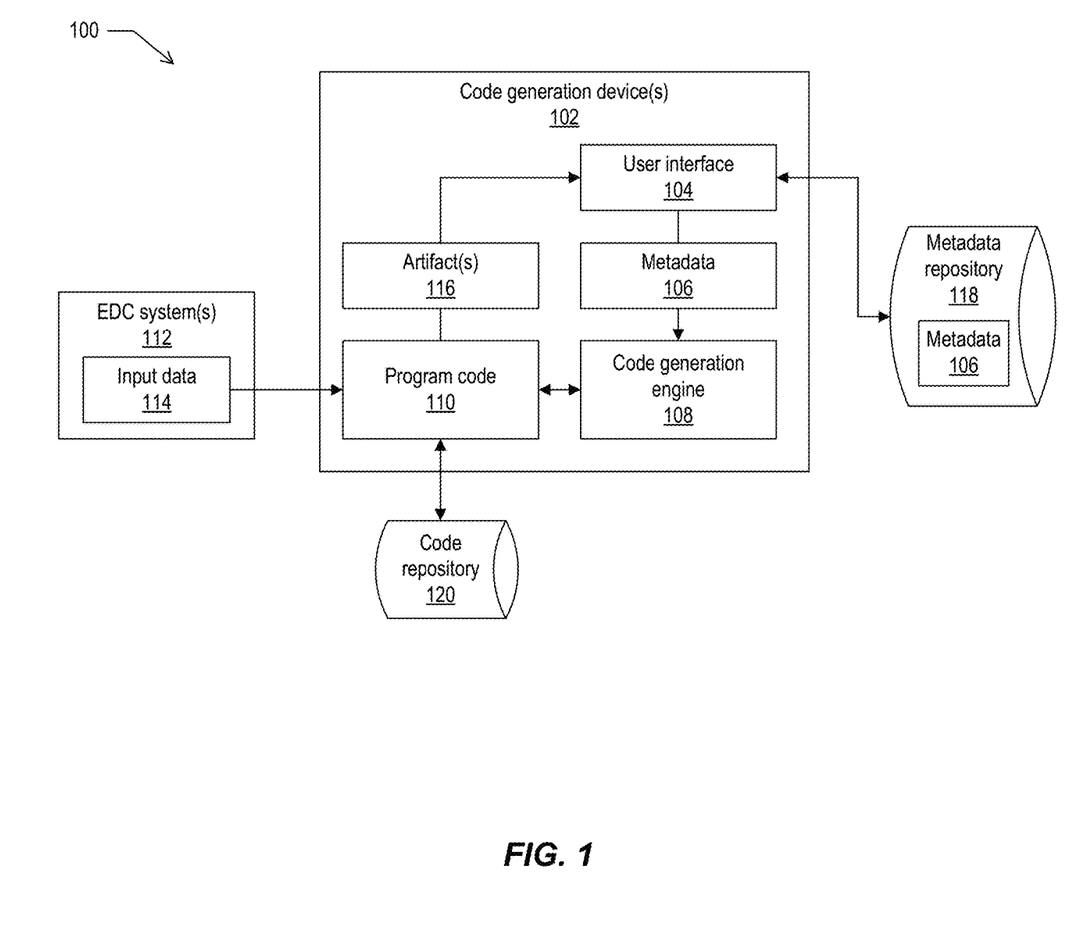
FIG. 1 depicts an example system for code generation and execution, according to implementations of the present disclosure.

FIG. 1 depicts an example system 100 for code generation and execution, according to implementations of the present disclosure. As shown in the example of FIG. 1, the system may include one or more code generation devices 102. The code generation device(s) 102 may include any suitable number and type of computing device. The code generation device(s) 102 may execute or otherwise provide access to a user interface (UI) 104. The UI 104 may be employed to specify metadata 106 to be used for code generation. In at least some implementations, a user can specify metadata 106, through the UI 104, to be used for code generation. For example, the user may use the UI 104 to identify a particular metadata file in the metadata repository 118. The system may retrieve the set of metadata in the identified metadata file from the repository 118, and use the metadata 106 to instruct the code generation engine 108. The metadata 106 may include inline code and/or reference(s) to code in the code repository 120. The inline code may be stored in the repository 118 with the metadata 106.

The metadata may be provided to a code generation engine 108, which generates program code 110 based on the metadata 106. The program code 110 may execute to create one or more artifacts 116. In some instances, the artifact(s) 116 may be communicated or otherwise provided to the UI 104, and the UI 104 may present the artifact(s) 116. In some instances, the artifact(s) 116 may be communicated over one or more networks for use by and/or presentation on other devices. The artifact(s) 116 may also be stored in data storage that is local or remote to the code generation device(s) 102.

The program code 110 may receive input data 114, and perform one or more operations based on the input data 114 to generate the artifact(s) 116. In some implementations, the input data 114 may be data generated through one or more clinical trials. The input data 114 may be stored in a data repository that is local or remote with respect to the code generation device(s) 102. In the example of FIG. 1, the input data 114 is stored on one or more or electronic data capture (EDC) systems 112 that receive the input data 114 during and/or after the input data 114 is generated through one or more clinical trials. The program code 110 may retrieve the input data 114 from the EDC system(s) 112, e.g., over one or more networks. As used herein, a clinical trial may include any appropriate type of test, experiment, study, evaluation, and/or other activity performed to measure or otherwise determine the effect, on human or animal test subjects, of a drug, medical device (e.g., biomedical device), treatment regimen, dietary regimen, dietary supplement, course of therapy, or other subject of investigation. A clinical trial may be performed by a government agency, private entity (e.g., business), and/or public entity.

In some implementations, the metadata 106 may be retrieved from a metadata repository 118 and provided to the code generation engine 108. For example, a user may use the UI 104 to specify a particular metadata file that is stored in the metadata repository 118. The file may be retrieved from the metadata repository 118 and provided to the engine 108 for use in code generation. In some implementations, at least a portion of the program code 110 may be stored in a code repository 120. For example, the metadata 106 may reference a routine that is stored, e.g., in a library, in the code repository 120. In such examples, code generation may include retrieving the referenced routine from the code repository 120 for inclusion in the generated program code 110. In some implementations, the metadata 106 may include, e.g., inline in the metadata, code to be included in the program code 110. In such instances, the code may be retrieved from the metadata 106 and added to the program code 110 during code generation. After code generation, the inline code that is retrieved from the metadata 106 may be stored in the code repository 120, such that subsequently used sets of metadata 106 may include a reference to the stored code in the library instead of including the code itself inline. Accordingly, over time as the library becomes more well-developed and more routines are stored in the library, the metadata may become smaller in size as it includes more references to library routines instead of inline code. The routines stored in the library may be described as utility macros that perform particular operations on data. The generated code may include one or more of the following: code that is generated based upon instructions in the metadata (e.g., not referencing any code from the code repository and not including inline code in the metadata); code that is included inline in the metadata, such that the engine retrieves the code from the metadata and inserts the code into the final generated code; and/or code that is stored in the code repository and referenced in the metadata, such that the engine retrieves the code from the repository and inserts it into the generated code. In some instances, the code that is present in the code repository is a self-configuring routine that uses instructions in the metadata to configure itself for use in the final generated code.

In some implementations, the engine 108 may generate the program code 110, and the program code 110 may be stored in the code repository 120 for re-use during a subsequent analysis. The metadata repository 118 and/or code repository 120 may be internal storage on the code generation device(s) 102, or may be external to the code generation device(s) 102 and accessible over one or more networks, external busses, etc.

Figure 2:
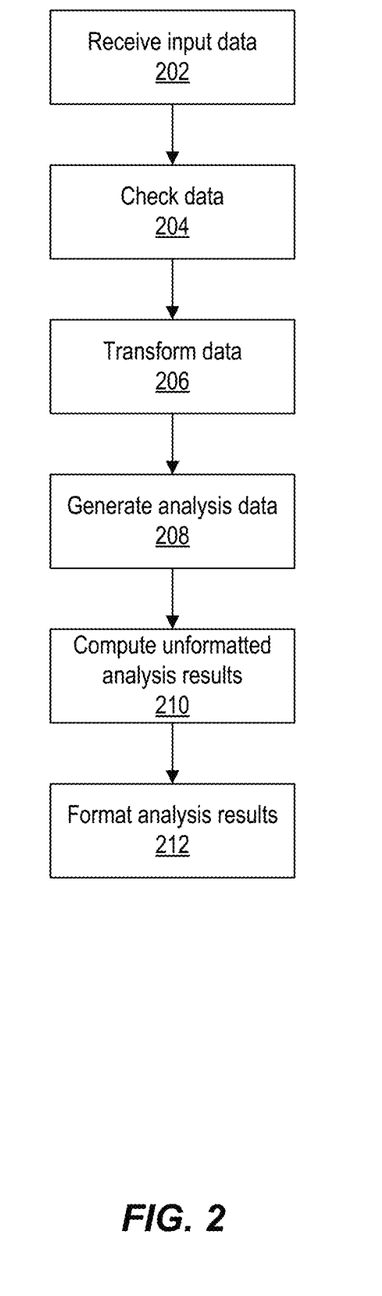
FIG. 2 depicts a flow diagram of an example process for analyzing data generated through clinical trial(s), according to implementations of the present disclosure.

FIG. 2 depicts a flow diagram of an example process for analyzing data generated through clinical trial(s), according to implementations of the present disclosure. The example process shown in FIG. 2 may be performed, in whole or in part, by the program code 110 that is generated by the engine 108.

The input data 114 is received (202). The input data 114 (e.g., the raw data) may be collected for the various subjects in a clinical study, and may be stored in and retrieved from an EDC system as described above. In some implementations, the input data 114 is checked in one or more data check reports (204), e.g., for cleanliness, prior to further processing and analysis. For example, the data check reports may identify data that is clearly erroneous or anomalous compared to the other data or compared to expected results. For example, a data check may verify that no male subjects in the clinical trial are identified as pregnant, or that no subject who is identified as having have had a blood sample drawn is missing a blood laboratory results report. The data checking may ensure that the data values in the EDC system accurately reflect the data values that were collected, such that there were no mistakes made in recording in the EDC system the data values presented by the subjects. Each data check report may be output as an artifact 116 to be used by data managers or other individuals who are responsible for the accuracy of the input data to be used for analysis and reporting. In some instances, certain actions may be performed to clean the input data before it is used in data analysis. Cleaning may include removing data that is identified as erroneous and/or anomalous in some way. In some instances, the cleaning of the data may be performed by the EDC system(s) 112. After this step, the data may be described as validated and/or verified, in implementations where checking the data includes determining whether the data is acceptable for further processing.

In some implementations, the input data 114 and/or checked data is transformed (206) to a (e.g., regulatory-required) format prior to further processing and analysis. For example, the data may be transformed to comply with a version of the Study Data Tabulation Model (SDTM) standard format for tabulation data, which is promulgated by the Clinical Data Interchange Standards Consortium (CDISC). The data formatting may output formatted data as an artifact 116.

The transformed input data may be used to generate (208) analysis data, which may be output as an artifact 116. In some implementations, the analysis data may be created in a particular (e.g., regulatory-required) format, such as a version of the CDISC ADaM format. For example, generating the analysis data may include performing an analysis to detect a change from a baseline value, such that the analysis data indicates the variation of results compared to the baseline. A baseline result, e.g., for blood chemistry, physiological state, or other characteristic, may be determined prior to giving a treatment to a subject. The input data may then be collected after the treatment has been applied, and operation(s) may compute the change, if any, from baseline at each stage. The derived analysis data may show the difference between the input data and the baseline result, if any difference is exhibited.

In some instances, the collected data is transformed to the SDTM format to provide the collected data in a standard form to a regulatory agency or other entity. The SDTM format provides a standard with respect to the data structure, the data nomenclature, and the data terminology. The SDTM format of the data is a transformation of the collected data to a new format, called the tabulation format. The regulatory agency may consume the collected data in a standard format so that it can use standard software routines to examine the data, regardless of the study or the biopharmaceutical company from which the data came. In the analysis process, analysis data sets are created from the SDTM data, and the analysis data sets may include a combination of the collected data and new data derived from the collected data. The change from baseline data is an example of this. The analysis datasets may be input to analysis software that computes additional analysis results. The analysis software might, for example, compute the statistical significance of observations made about the analysis data. The analysis results may be communicated or otherwise provided for presentation in formatted analysis reports. As another example of analysis data, some analyses may be run on a subset of the full subject population and other analyses on a different subset of the subject population. These subsets, or sub-populations, may be defined by rules. The analysis data may include a set of derived population flags that may be computed according to the rules being applied to the collected data, and that may indicate the sub-populations in which each subject is included. The analysis datasets may be generated in the ADaM format so that the regulatory agency can use its routines to examine the analysis data and check the analysis results, regardless of the origin of the analysis data.

The analysis data may be employed to compute (210) unformatted analysis results. The unformatted analysis results may then be formatted (212) to create a formatted analysis report, which may be provided as an artifact 116. For example, a formatted analysis report may include tables, figures, listings, and/or other types of output. As a particular example, a report may include a table that shows a change from baseline analysis on lab results. Such a table may compare results of applying a treatment to multiple treatment groups in which some group(s) of subjects receive a drug and others receive a placebo. The table may show the results of lab tests across different treatment groups over time, indicating the safety and/or efficacy of the drug, for example. A table may be an arrangement of data in any suitable number of rows and columns. A figure may present data in a graphical form, such as a scatter plot or histogram (e.g., in two dimensions), a linear graph, a bar graph, a pie graph, a multi-dimensional surface graph, etc. A listing may list data subjects by subject and/or time at multiple points in time.

Any or all of the operations shown in FIG. 2 may be performed by the program code 110 generated by the engine 108. The output of one or more of the operations of FIG. 2, such as the checked data, the transformed data, the analysis data, the unformatted analysis results, and/or the formatted analysis report(s), may be an artifact 116 that is created as output by the executing program code 110. The various artifact(s) 116 may be presented through a UI 104 executing on a computing device such as the code generation device(s) 102.

The metadata 106 may describe the artifact(s) 116 to be output by the program code 110, the various operation(s) to be performed to create the artifact(s) 116, and/or the input data 114 to be input to the program code 110. For example, each set of input data 114 to be used may be indicated by a file location in the EDC system(s) 112. The metadata 106 may describe how multiple input data sets are to be joined or otherwise combined in the analysis, or filtered to select a subset of the input data 114. The metadata 106 may describe various operation(s) that are to be performed to create the analysis variables from combined input data sets. The metadata 106 may also describe the analysis variables to be included in the analysis data. The metadata 106 may also specify the output artifact(s) 116 to be produced. In some instances, the metadata 106 may indicate the study name of the study that includes the output artifact(s) 116. In some instances, a particular study may pertain to multiple sets of artifact(s) 116. In general, the metadata 106 may describe a series of operations to be performed on the input data 114, and an order in which the operations are to be performed.

In some implementations, the code generation performed by the engine 108 is deterministic. For example, the engine 108 produces the same program code 110 in response to receiving the same metadata input, so long as any library routines used in the generated code have not changed. By employing the engine 108 to generate the program code 110, implementations achieve higher efficiency in resource utilization compared to traditional systems in which code is written manually for multiple studies.

In some implementations, the metadata repository 116 is a metadata management tool that includes one or more features usable to manage the metadata 106. Such a tool may be integrated with the metadata repository 118. The metadata 106 may include global metadata that is relevant to a plurality of studies. The metadata 106 may include project level metadata that is associated with a project that includes a subset of the plurality of studies. The metadata 106 may include study level metadata that is associated with a particular one of the plurality of studies. Accordingly, the metadata 106 may be stored in the repository 118 and/or otherwise managed as a hierarchy of metadata 106 that varies from less specific (e.g., global) to more specific (e.g., study specific). The metadata repository 118 may expose an interface, such as a web interface, application programming interface (API), or other interface, to enable the UI 104, code generation engine 108, and/or other processes to readily access the metadata 106 stored in the repository 118.

Figure 3:
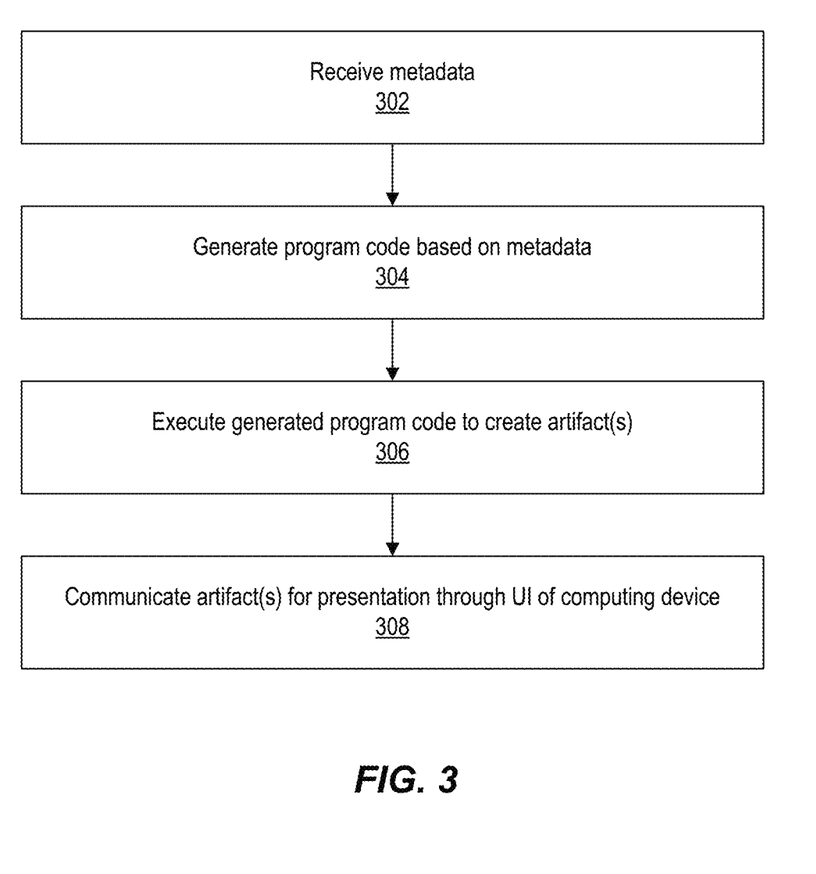
FIG. 3 depicts a flow diagram of an example process for code generation and execution, according to implementations of the present disclosure.

FIG. 3 depicts a flow diagram of an example process for code generation and execution, according to implementations of the present disclosure. Operations of the process may be performed by one or more of the code generation engine 108, the UI 104, the program code 110, and/or other software executing on the code generation device(s) 102, the EDC system(s) 112, or elsewhere.

The metadata 106 may be received (302). As described above, the metadata 106 may be specified through the UI 104, e.g., as a particular file name and/or file location in the repository 118, and the metadata 106 may be retrieved from the repository 118 and provided to the engine 108.

The engine 108 may generate (304) the program code 110 based on the metadata 106 as described above. Code generation is described in further detail below with reference to FIG. 4.

The generated program code 110 may be executed (306) to create the various artifact(s) 116 specified in the metadata 106. In some implementations, the program code 110 may be completely generated prior to its execution. In some implementations, the program code 110 may be executed as it is being generated.

The artifact(s) 116 created through execution of the program code 110 may be communicated over one or more networks or otherwise provided to a UI 104 that is executing on a computing device. The UI 104 may present the artifact(s) 116. In some implementations, the engine 108 may receive information regarding which study is being analyzed. In such examples, the artifact(s) 116 may include an indication of the particular study.

Figure 4:
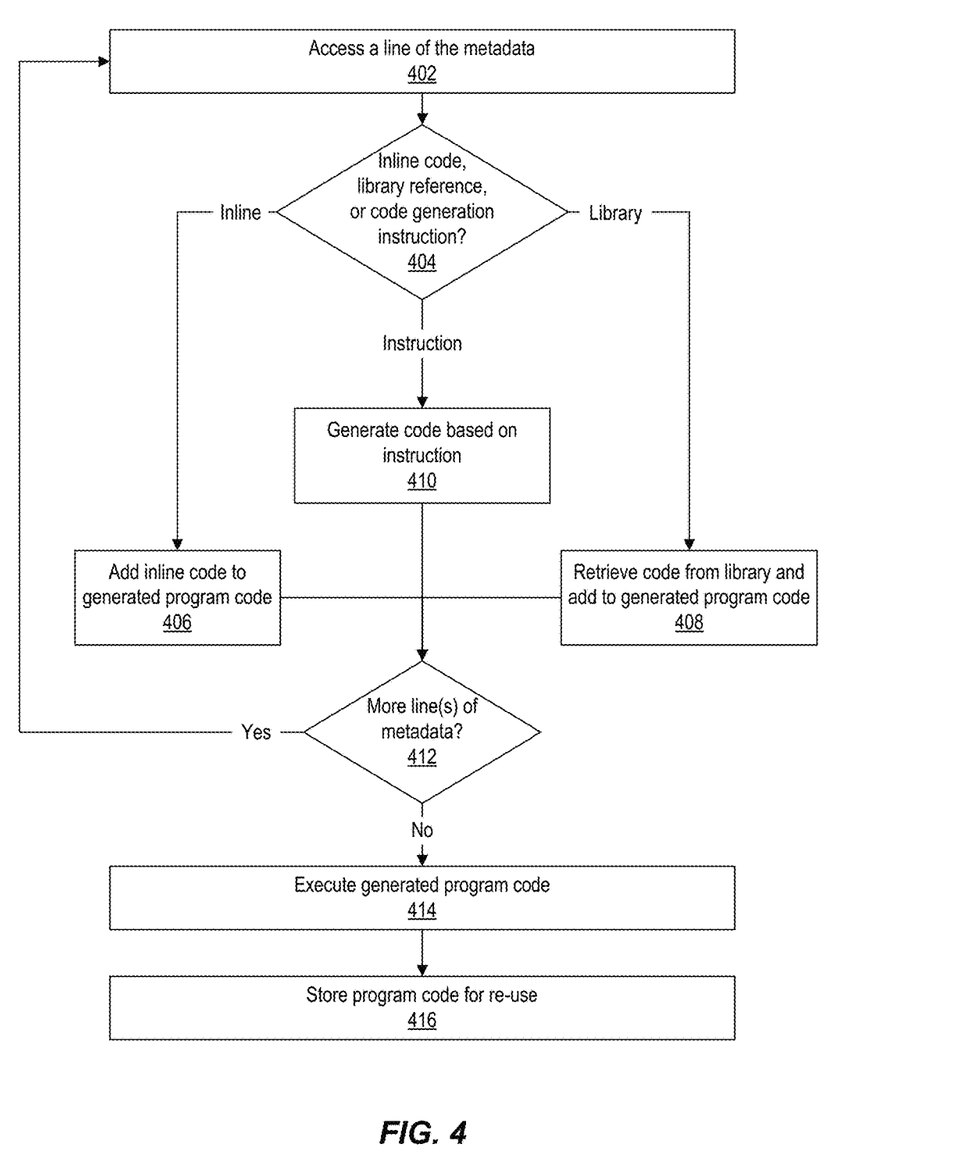
FIG. 4 depicts a flow diagram of an example process for code generation, according to implementations of the present disclosure.

FIG. 4 depicts a flow diagram of an example process for code generation, according to implementations of the present disclosure. Operations of the process may be performed by one or more of the code generation engine 108, the UI 104, the program code 110, and/or other software executing on the code generation device(s) 102, the EDC system(s) 112, or elsewhere.

After receiving the metadata 106, a first line of the metadata 106 may be accessed (402). A determination may be made (404) whether the line includes inline code, a reference to a library routine, or a code generation instruction. If the line includes inline code, the inline code may be extracted from the metadata 106 and added (406) to the generated program code 110. If the line includes a reference to a library routine, the code may be retrieved (408) from the library and added to the generated program code 110. If the line includes a code generation instruction, the code may be generated (410) based on (e.g., through execution of) the instruction. For example, the line of metadata may indicate a network address and/or file location where the input data is located, and the engine may use that information to generate a data library reference in the appropriate syntax of the software system that is to execute the generated program code. As another example, the line of metadata may provide the title and/or footnote of a table to be created, and the engine may generate a title or footnote statement in the appropriate syntax of the software system that is to execute the generated program code.

After processing the line of metadata 106, a determination may be made (412) whether the metadata 106 includes more line(s) to be processed. If more lines of metadata are present, the method may process the next line of metadata 106. If no more lines of metadata are present, the generated program code 110 may be executed (414). In some implementations, the generated program code 110 may be stored (416), e.g., in the code repository 120, for subsequent re-use as appropriate. For example, same metadata 106 for a same study may use the previously generated program code 110 instead of regenerating the program code 110.

Table 1 below lists example metadata 106 for artifact creation, which may be employed by the engine 108, according to at least some implementations.

TABLE 1

| Sequence Number | Description | Macro Name | Macro Parameter Name | Macro Parameter Value |
|---|---|---|---|---|
| 1 | Setup library step to create libname, filename, macro variables. | frm_setup_code_generator.sas | code_type | setup |
| 2 | Create temporary dataset containing joined domain and supplementary datasets | stgu_suppjoin.sas | domain | DM |

TABLE 1-continued

| Sequence Number | Description | Macro Name | Macro Parameter Name | Macro Parameter Value |
|---|---|---|---|---|
| 2 | Create temporary dataset containing joined domain and supplementary datasets | stgu_suppjoin.sas | output_dataset | work.DMSUPP |
| 2 | Create temporary dataset containing joined domain and supplementary datasets | stgu_suppjoin.sas | suppvars | RACEOR |
| 2 | Create temporary dataset containing joined domain and supplementary datasets | stgu_suppjoin.sas | wherecls | %str(ARM ne 'Screen Failure') |
| 3 | Create dataset containing treatment start and end dates for ADSL | stau_adam_adsl_treat_dates.sas | output_dsname | trtdates |
| 4 | Joining Code Generator to derive the target dataset by reading the Mapping Joins Metadata | frm_mapping_joins_code_generator.sas | code_type | joins |
| 5 | Mapping Code Generator to derive the target variables by reading the Mapping Rules Metadata | frm_mapping_rules_code_generator.sas | output_dsname | adsl |
| 6 | Sort final ADSL dataset | stgu_sort_dataset.sas | input_dsname | adsl |
| 6 | Sort final ADSL dataset | stgu_sort_dataset.sas | output_dsname | adam.adsl |
| 6 | Sort final ADSL dataset | stgu_sort_dataset.sas | sortvars | usubjid |
| 7 | Final output step | frm_output_code_generator.sas | in_out_dsname | adam.adsl |
| 8 | Cleanup | stgu_cleanup.sas | | |

Table 2 below lists example metadata 106 for mapping rules, which may be employed by the engine 108, according to at least some implementations. Though not shown in the example Table 2, in some instances one or more of the metadata lines may include a reference to code stored in a code repository (as described above).

TABLE 2

| Source Variable Name | Rule Type | Derivation Type | Target Dataset Name | Target Variable Name | Inclusion | Code Name | Code List ID |
|---|---|---|---|---|---|---|---|
| STUDYID | S | | ADSL | STUDYID | Y | | |
| USUBJID | S | | ADSL | USUBJID | Y | | |
| SUBJID | S | | ADSL | SUBJID | Y | | |
| SITEID | S | | ADSL | SITEID | Y | | |
| COUNTRY | S | | ADSL | COUNTRY | Y | | |
| INVNAM | S | | ADSL | INVNAM | Y | | |
| SITEID | D | CL | ADSL | SITEGRy | N | | |
| SITEGRy | D | CL | ADSL | SITEGRyN | N | | |
| REGIONy | D | CL | ADSL | REGIONy | N | | |
| AGE | S | | ADSL | REGIONyN | N | | |
| AGEU | S | | ADSL | AGE | Y | | |
| | | | ADSL | AGEU | Y | | |
| | | | ADSL | AGEGR1 | N | | |
| | | | ADSL | AGEGR1N | N | | AGEGR1N |
| AGE | D | GV | ADSL | AGEGRy | N | | |
| AGEGRy | D | CL | ADSL | AGEGRyN | N | | AGEGR1N |
| BRTHDT | D | SC | ADSL | AAGE | N | %ostgu_calculate_age(invarname=<age_at_date>,outvarname=AAGE); | |
| | D | AS | ADSL | AAGEU | N | | |
| | D | AS | ADSL | AAGEGR1 | N | | |
| | | | ADSL | AAGEGR1N | N | | AAGEGR1N |
| AAGE | D | GV | ADSL | AAGEGRy | N | | |
| AAGEGRy | D | CL | ADSL | AAGEGRyN | N | | AAGEGR1N |
| BRTHDT | D | SC | ADSL | AAGEw | N | %ostgu_calculate_age(invarname=<age_at_date_w>,outvarname=AAGEw); | |
| | D | AS | ADSL | AAGEwU | N | | |
| AAGEw | D | GV | ADSL | AAGEwGy | N | | |
| AAGEwGRy | D | CL | ADSL | AAGEwGyN | N | | |
| | | | ADSL | HEIGHTBL | N | | |
| | | | ADSL | WEIGHTBL | N | | |
| | | | ADSL | BMIBL | N | | |
| | | | ADSL | FASFL | N | | |
| | | | ADSL | SAFFL | N | | |
| | | | ADSL | ITTFL | N | | |
| | | | ADSL | PPROTFL | N | | |
| | | | ADSL | COMPLFL | N | | |

TABLE 2-continued

| Source Variable Name | Rule Type | Derivation Type | Target Dataset Name | Target Variable Name | Inclusion | Code Name | Code List ID |
|---|---|---|---|---|---|---|---|
| RANDDT | D | SC | ADSL | RANDFL | N | If not missing(randdt) then RANDFL = 'Y'; else RANDFL = 'N'; | |
| ENRLDT | D | SC | ADSL | ENRLFL | N | If not missing(enrldt) then ENRLFL = 'Y'; else ENRLFL = 'N'; | |
| | D | SC | ADSL | VACCFL | N | if subjpres_presex = 'Y' and elimvaccne ='Y' then VACCFL='Y'; | |
| ARM | S | | ADSL | ARM | Y | | |
| ARMCD | S | | ADSL | ARMCD | Y | | |
| ACTARM | S | | ADSL | ACTARM | Y | | |
| ACTARMCD | S | | ADSL | ACTARMCD | Y | | |
| ARM | D | CL | ADSL | TRT01P | N | | TRTNAMES |
| TRTSDT | S | | ADSL | TRTSDT | Y | | |
| | | | ADSL | TRTSTM | N | | |
| | | | ADSL | TRTSDTM | N | | |
| | | | ADSL | TRTSDTF | N | | |
| | | | ADSL | TRTSTMF | N | | |
| TRTEDT | S | | ADSL | TRTEDT | Y | | |
| | | | ADSL | TRTETM | N | | |
| | | | ADSL | DCPxxRS | N | | |
| | | | ADSL | DCPxxRSP | N | | |
| BRTHDTC | S | | ADSL | BRTHDTC | Y | | |
| BRTHDTC | D | SC | ADSL | BRTHDT | Y | if length(brthdtc)ge 10 then BRTHDT=input(brthdtc,yymmdd10.); else if length(brthdtc)=7 then BRTHDT=mdy(input(substr(brthdtc,6,2),2.),15,input(substr(brthdtc,1,4),4.)); else if length(brthdtc)=4 then BRTHDT=mdy(6,30,input(brthdtc,4.)); | |
| BRTHDTC | D | SC | ADSL | BRTHDTF | N | if length(brthdtc)=7 then BRTHDTF='D'; else if length(brthdtc)=4 then BRTHDTF='M'; | |
| | | | ADSL | RFICDTC | | | |

Figure 5:
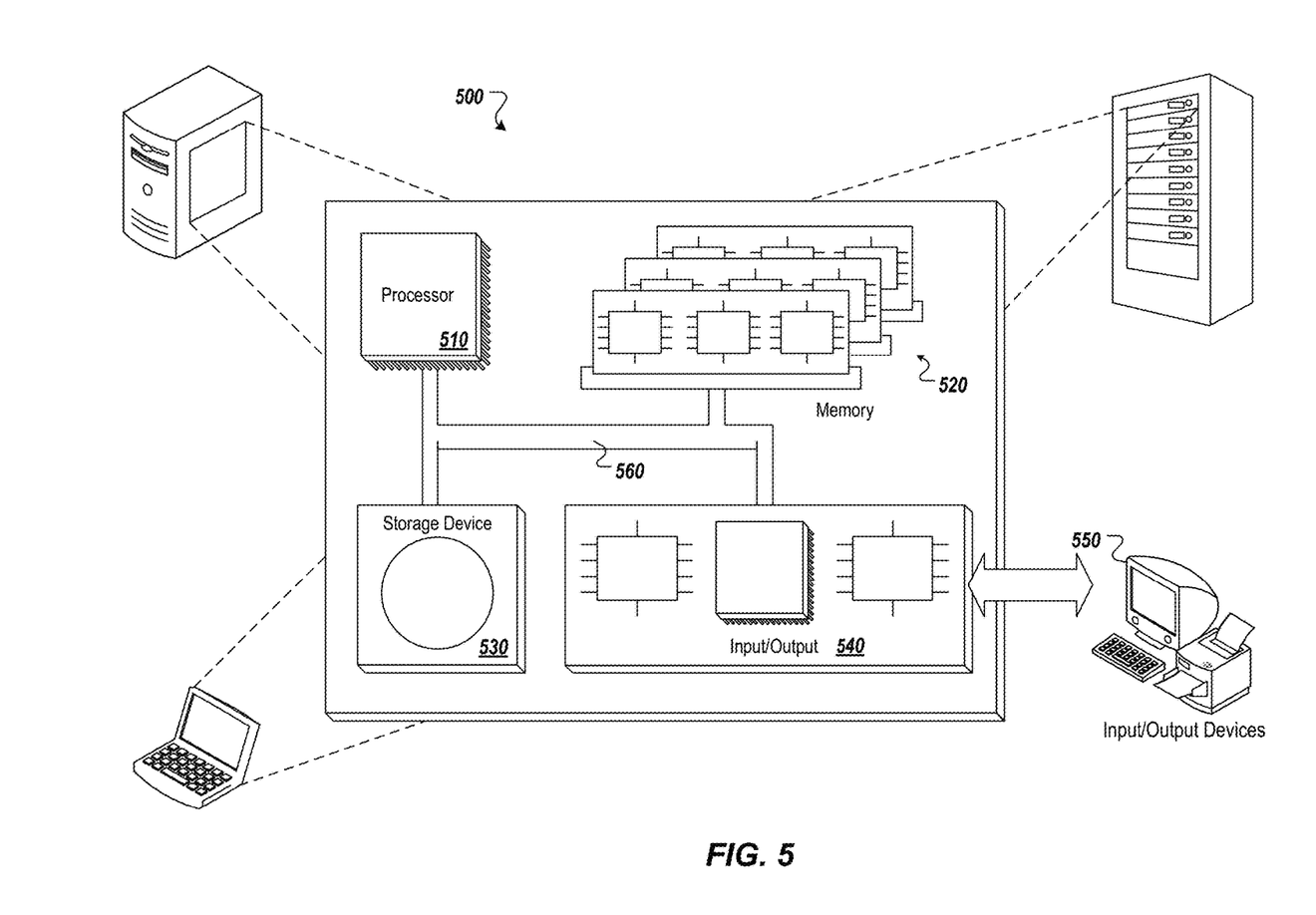
FIG. 5 depicts an example computing system, according to implementations of the present disclosure.

FIG. 5 depicts an example computing system, according to implementations of the present disclosure. The system 500 may be used for any of the operations described herein with respect to the various implementations discussed herein. For example, the system 500 may be included, at least in part, in one or more of the code generation device(s) 102, the EDC system(s) 112, the metadata repository 118, the code repository, 120, and/or other computing device(s) or system(s) described herein. The system 500 may include one or more processors 510, a memory 520, one or more storage devices 530, and one or more input/output (I/O) devices 550 controllable via one or more I/O interfaces 540. The various components 510, 520, 530, 540, or 550 may be interconnected via at least one system bus 560, which may enable the transfer of data between the various modules and components of the system 500.

The processor(s) 510 may be configured to process and execute machine-readable instructions within the system 500. The processor(s) 510 may include single-threaded processor(s), multi-threaded processor(s), or both. The processor(s) 510 may be configured to process/execute instructions stored in the memory 520 or on the storage device(s) 530. For example, the processor(s) 510 may execute instructions for the various software module(s) described herein. The processor(s) 510 may include hardware-based processor(s) each including one or more cores. The processor(s) 510 may include general purpose processor(s), special purpose processor(s), or both.

The memory 520 may store information within the system 500. In some implementations, the memory 520 includes one or more computer-readable media. The memory 520 may include any number of volatile memory units, any number of non-volatile memory units, or both volatile and non-volatile memory units. The memory 520 may include read-only memory, random access memory, or both. In some examples, the memory 520 may be employed as active or physical memory by one or more executing software modules.

The storage device(s) 530 may be configured to provide (e.g., persistent) mass storage for the system 500. In some implementations, the storage device(s) 530 may include one or more computer-readable media. For example, the storage device(s) 530 may include a floppy disk device, a hard disk device, an optical disk device, or a tape device. The storage device(s) 530 may include read-only memory, random access memory, or both. The storage device(s) 530 may include one or more of an internal hard drive, an external hard drive, or a removable drive.

One or both of the memory 520 or the storage device(s) 530 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 500. In some implementations, the CRSM may include a data store that provides storage of computer-readable instructions or other information in a non-transitory format. The CRSM may be incorporated into the system 500 or may be external with respect to the system 500. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) 510 and the memory 520 may be supplemented by, or incorporated into, one or more application-specific integrated circuits (ASICs).

The system 500 may include one or more I/O devices 550. The I/O device(s) 550 may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) 550 may also include one or more output devices such as a display, LED(s), an audio output device (e.g., a speaker), a printer, a haptic output device, and so forth. The I/O device(s) 550 may be physically incorporated in one or more computing devices of the system 500, or may be external with respect to one or more computing devices of the system 500.

The system 500 may include one or more I/O interfaces 540 to enable components or modules of the system 500 to control, interface with, or otherwise communicate with the I/O device(s) 550. The I/O interface(s) 540 may enable information to be transferred in or out of the system 500, or between components of the system 500, through serial communication, parallel communication, or other types of communication. For example, the I/O interface(s) 540 may comply with a version of the RS-232 standard for serial ports, or with a version of the IEEE 1284 standard for parallel ports. As another example, the I/O interface(s) 540 may be configured to provide a connection over Universal Serial Bus (USB) or Ethernet. In some examples, the I/O interface(s) 540 may be configured to provide a serial connection that is compliant with a version of the IEEE 1394 standard.

The I/O interface(s) 540 may also include one or more network interfaces that enable communications between computing devices in the system 500, or between the system 500 and other network-connected computing systems. The network interface(s) may include one or more network interface controllers (NICs) or other types of transceiver devices configured to send and receive communications over one or more communication networks using any network protocol.

Computing devices of the system 500 may communicate with one another, or with other computing devices, using one or more communication networks. Such communication networks may include public networks such as the internet, private networks such as an institutional or personal intranet, or any combination of private and public networks. The communication networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 500 may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor may receive instructions and data from a read only memory or a random access memory or both. Elements of a computer can include a processor for performing instructions and one or more memory devices for storing instructions and data. Generally, a computer may also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical user interface or a web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some examples be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

The invention claimed is:

1. A computer-implemented method for analyzing clinical trial data, the method performed by at least one processor, the method comprising:
   accessing, by the at least one processor, metadata that describes:
     an input data set for a clinical trial,
     at least one artifact to be provided as output, and
     at least one operation to be performed on the input data set to create the at least one artifact, wherein the metadata is arranged hierarchically to include at least two of:
       global metadata that is associated with a plurality of studies,
       project level metadata that is associated with a project that includes a subset of the plurality of studies, and
       study level metadata that is associated with one of the plurality of studies;
   generating, by the at least one processor, based on the metadata, program code that performs the at least one operation to create the at least one artifact, wherein the at least one operation includes:
     detecting a difference between at least one element of the input data set and a respective baseline value,
     generating analysis data that includes both the input data set and the detected difference, and
     providing the analysis data as input to analysis software that generates the at least one artifact,
     wherein the generating of the program code includes retrieving at least a first portion of the program code from a code repository based on a reference included in the metadata;
   executing, by the at least one processor, the program code to perform the at least one operation on the input data set, wherein the executing of the program code creates the at least one artifact based on the performing the at least one operation, and wherein the at least one artifact indicates the detected difference between the at least one element of the input data and the respective baseline value, wherein the at least one operation includes:
     retrieving, from an electronic data capture (EDC) system, the input data set that includes raw data generated through the clinical trial,
     performing a quality check on the raw data,
     determining analysis data based on the raw data, and
     determining the at least one artifact based on the analysis data, and
     wherein the at least one artifact includes at least one report that describes a result of one or more of cleaning, checking, and formatting the data during at least two stages in the handling of the data; and
   communicating, by the at least one processor, the at least one artifact for presentation through a user interface of a computing device.

2. The method of claim 1, wherein the generating of the program code further includes executing at least one instruction included in the metadata to generate at least a second portion of the program code.

3. The method of claim 2, further comprising:
   storing, by the at least one processor, the generated second portion of the program code in the code repository.

4. The method of claim 1, wherein the generating of the program code further includes retrieving, from the metadata, at least a third portion of the program code that is included inline in the metadata.

5. The method of claim 4, further comprising:
   storing, by the at least one processor, the retrieved third portion of the program code in the code repository.

6. The method of claim 1, wherein the at least one artifact includes one or more of a table, a figure, and a listing of data.

7. The method of claim 1, wherein the at least one operation further includes
   transforming the raw data to a first standard format; and
   transforming the analysis data to a second standard format.

8. The method of claim 1, wherein:
   the program code is associated with an individual study of the plurality of studies performed during the clinical trial;
   the input data set includes data associated with the individual study; and
   the at least one artifact is associated with the individual study.

9. The method of claim 1, wherein the program code is generated and executed by a same code generation engine.

10. A system for analyzing clinical trial data, the system comprising:
    at least one processor; and
    a memory communicatively coupled to the at least one processor, the memory storing instructions which, when executed, cause the at least one processor to perform actions comprising:
      accessing metadata that describes:
        an input data set for a clinical trial,
        at least one artifact to be provided as output, and
        at least one operation to be performed on the input data set to create the at least one artifact, wherein the metadata is arranged hierarchically to include at least two of:
          global metadata that is associated with a plurality of studies, project level metadata that is associated with a project that includes a subset of the plurality of studies, and study level metadata that is associated with one of the plurality of studies;

generating, based on the metadata, program code that performs the at least one operation to create the at least one artifact, wherein the at least one operation includes:

detecting a difference between at least one element of the input data and a respective baseline value, generating analysis data that includes both the input data set and the detected difference, and providing the analysis data as input to analysis software that generates the at least one artifact, wherein the generating of the program code includes retrieving at least a first portion of the program code from a code repository based on a reference included in the metadata;

executing the program code to perform the at least one operation on the input data set, wherein the executing of the program code creates the at least one artifact based on the performing the at least one operation, and wherein the at least one artifact indicates the detected difference between the at least one element of the input data and the respective baseline value, wherein the at least one operation includes:

retrieving, from an electronic data capture (EDC) system, the input data set that includes raw data generated through the clinical trial, performing a quality check on the raw data, determining analysis data based on the raw data, and determining the at least one artifact based on the analysis data, and wherein the at least one artifact includes at least one report that describes a result of one or more of cleaning, checking, and formatting the data during at least two stages in the handling of the data; and communicating the at least one artifact for presentation through a user interface of a computing device.

11. The system of claim 10, wherein the generating of the program code further includes executing at least one instruction included in the metadata to generate at least a second portion of the program code.

12. The system of claim 11, the actions further comprising:

storing the generated second portion of the program code in the code repository.

13. The system of claim 10, wherein the generating of the program code further includes retrieving, from the metadata, at least a third portion of the program code that is included inline in the metadata.

14. The system of claim 13, the actions further comprising:

storing the retrieved third portion of the program code in the code repository.

15. The system of claim 10, wherein the at least one operation further includes transforming the raw data to a first standard format; and transforming the analysis data to a second standard format.

16. The system of claim 10, wherein:

the program code is associated with an individual study of the plurality of studies performed during the clinical trial;

the input data set includes data associated with the individual study; and the at least one artifact is associated with the individual study.

17. The system of claim 10, wherein the program code is generated and executed by a same code generation engine.

18. One or more non-transitory computer-readable storage media storing instructions which, when executed, cause at least one processor to perform actions for analyzing clinical trial data, the actions comprising:

accessing metadata that describes:

an input data set for a clinical trial, at least one artifact to be provided as output, and at least one operation to be performed on the input data set to create the at least one artifact, wherein the metadata is arranged hierarchically to include at least two of:

global metadata that is associated with a plurality of studies, project level metadata that is associated with a project that includes a subset of the plurality of studies, and study level metadata that is associated with one of the plurality of studies;

generating, based on the metadata, program code that performs the at least one operation to create the at least one artifact, wherein the at least one operation includes:

detecting a difference between at least one element of the input data and a respective baseline value, generating analysis data that includes both the input data set and the detected difference, and providing the analysis data as input to analysis software that generates the at least one artifact, wherein the generating of the program code includes retrieving at least a first portion of the program code from a code repository based on a reference included in the metadata;

executing the program code to perform the at least one operation on the input data set, wherein the executing of the program code creates the at least one artifact based on the performing the at least one operation, and wherein the at least one artifact indicates the detected difference between the at least one element of the input data and the respective baseline value, wherein the at least one operation includes:

retrieving, from an electronic data capture (EDC) system, the input data set that includes raw data generated through the clinical trial, performing a quality check on the raw data, determining analysis data based on the raw data, and determining the at least one artifact based on the analysis data, and wherein the at least one artifact includes at least one report that describes a result of one or more of cleaning, checking, and formatting the data during at least two stages in the handling of the data; and communicating the at least one artifact for presentation through a user interface of a computing device.

* * * * *